United States Patent
Iida et al.

(10) Patent No.: US 8,154,719 B2
(45) Date of Patent: Apr. 10, 2012

(54) MASK INSPECTION APPARATUS

(75) Inventors: Susumu Iida, Kanagawa (JP); Shunsaku Kubota, Kanagawa (JP)

(73) Assignees: NuFlare Technology, Inc., Numazu-shi (JP); Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 316 days.

(21) Appl. No.: 12/402,878

(22) Filed: Mar. 12, 2009

(65) Prior Publication Data

US 2009/0244530 A1    Oct. 1, 2009

(30) Foreign Application Priority Data

Mar. 31, 2008    (JP) .................. 2008-092253

(51) Int. Cl.
*G01N 21/00* (2006.01)
(52) U.S. Cl. .............. 356/237.5; 356/237.1
(58) Field of Classification Search .... 356/237.1–237.6, 356/243.4–243.8; 250/370.01, 370.14, 336.1, 250/397, 208.1, 239, 396 R, 214.1; 257/443, 257/448, 457–459, 676; 345/207
See application file for complete search history.

(56) References Cited

U.S. PATENT DOCUMENTS

| | | | |
|---|---|---|---|
| 5,150,180 A * | 9/1992 | Yama | 357/29 |
| 5,923,034 A * | 7/1999 | Ogasawara et al. | 250/311 |
| 7,157,720 B2 * | 1/2007 | Chao et al. | 250/397 |
| 7,507,944 B1 * | 3/2009 | Arnzen et al. | 250/208.1 |

FOREIGN PATENT DOCUMENTS

| | | |
|---|---|---|
| JP | 4-53155 | 2/1992 |
| JP | 7-22068 | 1/1995 |
| JP | 7-72011 | 3/1995 |
| JP | 8-94338 | 4/1996 |
| JP | 2000-321394 | 11/2000 |
| JP | 2002-71876 | 3/2002 |
| JP | 2002-166899 | 6/2002 |

OTHER PUBLICATIONS

A.R. Smith, et al., "Radiation events in astronomical CCD images", SPIE 4669, 172-183 (2002) (Electronic Imaging 2002), LBNL-49316, Jan. 23, 2002, 12 pages.

* cited by examiner

*Primary Examiner* — Tri T Ton
(74) *Attorney, Agent, or Firm* — Oblon, Spivak, McClelland, Maier & Neustadt, L.L.P.

(57) ABSTRACT

A lightweight and inexpensive mask inspection apparatus having highly efficient environmental radiation resistance is provided. The mask inspection apparatus is a mask inspection apparatus for inspecting for mask defects and includes a light source, an illuminating optical system configured to irradiate a mask with an inspection light emitted from the light source, a magnifying optical system configured to cause the inspection light with which the mask is irradiated to form an image as an optical image, and image sensor configured to acquire the optical image. The image sensor has an environmental radiation shielding member of heavy metal having a specific gravity equal to or greater than that of tantalum (Ta) at least on a side opposite to a receiving surface of a sensor chip.

16 Claims, 7 Drawing Sheets

MASK INSPECTION APPARATUS

CROSS-REFERENCE TO RELATED APPLICATION

This application is based upon and claims the benefit of priority from Japanese Patent Applications No. 2008-092253, filed on Mar. 31, 2008, the entire contents of which are incorporated herein by reference.

FIELD OF THE INVENTION

The present invention relates to a mask inspection apparatus, for example, a mask inspection apparatus for inspecting defects of masks for manufacturing semiconductor devices.

BACKGROUND OF THE INVENTION

In recent years, with higher integration and larger capacitance of large-scale integrated (LSI) circuits, the circuit line width required for semiconductor devices is becoming increasingly smaller. These semiconductor devices are manufactured by using an original pattern (also called a mask, photo mask, or reticle and hereinafter, referred to generically as a mask) to transfer the pattern onto a wafer by exposure in a reduced projection aligner, called a stepper, for circuit formation.

Improvement of die yields is indispensable to the manufacturing of LSI that requires a huge manufacturing cost. A leading cause that decreases yields is pattern defects of mask used for exposure and transfer of fine patterns onto a semiconductor wafer. As dimensions of LSI pattern formed on a semiconductor wafer become increasingly smaller in recent years, sizes of defects that need to be detected are becoming extremely small. Thus, a mask inspection apparatus that inspects for defects of masks used for the manufacturing of LSI needs to have high accuracy.

In the mask inspection apparatus, a mask surface is irradiated with an inspection light such as a coherent light and a reflected light or transmitted light thereof is collected by an image sensor to create images from collected data. At this point, the reflected light or transmitted light from the mask surface may be a very weak signal and thus, an image sensor with very high sensitivity is indispensable.

For an image sensor with very high sensitivity, environmental radiation such as cosmic rays and natural radiation could become noise sources. In such a case, it becomes impossible to distinguish between a signal caused by noise and that caused by defects of mask, affecting system performance significantly (See, for example, A. R. Smith et al., "Radiation events in astronomical CCD images", SPIE 4669, 172-183 (2002)).

JP-A 2002-166899 (KOKAI) discloses a space environment resistant container made of light and inexpensive aluminum material for storing electronic components.

SUMMARY OF THE INVENTION

A mask inspection apparatus in an embodiment of the present invention includes a light source, an illuminating optical system configured to irradiate a mask with an inspection light emitted from the light source, a magnifying optical system configured to cause the inspection light with which the mask is irradiated to form an optical image, an image sensor configured to acquire the optical image, wherein the image sensor has an environmental radiation shielding member of heavy metal at least on an opposite side of a receiving surface of a sensor chip.

A mask inspection apparatus in an embodiment of the present invention includes a light source, an illuminating optical system configured to irradiate a mask with an inspection light emitted from the light source, a magnifying optical system configured to cause the inspection light with which the mask is irradiated to form an optical image, and an image camera having an image sensor configured to acquire the optical image as a photo detector, wherein a frame of the image camera is formed from heavy metal having a specific gravity equal to or greater than that of tantalum (Ta).

According to the present invention, a lightweight and inexpensive mask inspection apparatus having highly efficient environmental radiation resistance can be provided.

DETAILED DESCRIPTION OF THE EMBODIMENTS

Embodiments of the present invention will be described below with reference to drawings. Simply heavy metal is herein a concept that includes, in addition to a single metal, alloys.

Cosmic rays include, in addition to $\alpha$ rays, $\beta$ rays, and $\gamma$ rays, muons. Moreover, each cosmic ray has a wide range of energy band and thus, it is most effective to install an apparatus deep underground, for example, at a site of mine to completely shield the image sensor from cosmic rays with a vast amount of energy. However, this method imposes great restrictions on apparatus installation.

Another method is to house an image sensor in a container of heavy metal such as lead. In this case, the thicker the heavy metal, the better the shield factor. Then, by setting the thickness of the heavy metal appropriately, cosmic rays in the desired energy band can be shielded, producing a considerable effect of removing the noise source from the image sensor to acquire even a weak signal. However, in order to house all attachment devices such as wires connected to the image sensor and a cooling unit in a heavy-metal container, the heavy-metal container will generally become large, causing a problem of increased weight and a higher price.

Currently, weight reduction and lower prices are challenges for a mask inspection apparatus and it is necessary to manufacture an apparatus in which a high-sensitivity image sensor is installed in reduced weight and at lower prices. Particularly for parts of an apparatus that are put on a vibration isolation base like an image sensor, weight reduction is needed to reduce natural vibration thereof.

The method of housing an image sensor or camera in a large container has, as described above, problems of heavy weight and high prices. Thus, it is necessary to use a small-sized and highly efficient shield while suppressing the use of heavy-metal material that is both heavy and expensive to a minimum as a container material.

First Embodiment

A mask inspection apparatus in the first embodiment of the present invention includes a light source, an illuminating optical system for irradiating a mask with an inspection light emitted from the light source, a magnifying optical system for causing the inspection light with which the mask is irradiated to form an optical image, and an image sensor for acquiring the optical image. In addition, the image sensor has an environmental radiation shielding member of heavy metal having a specific gravity equal to or greater than that of tantalum (Ta) at least on a side opposite to a receiving surface of a sensor chip of the image sensor.

Figure 2:
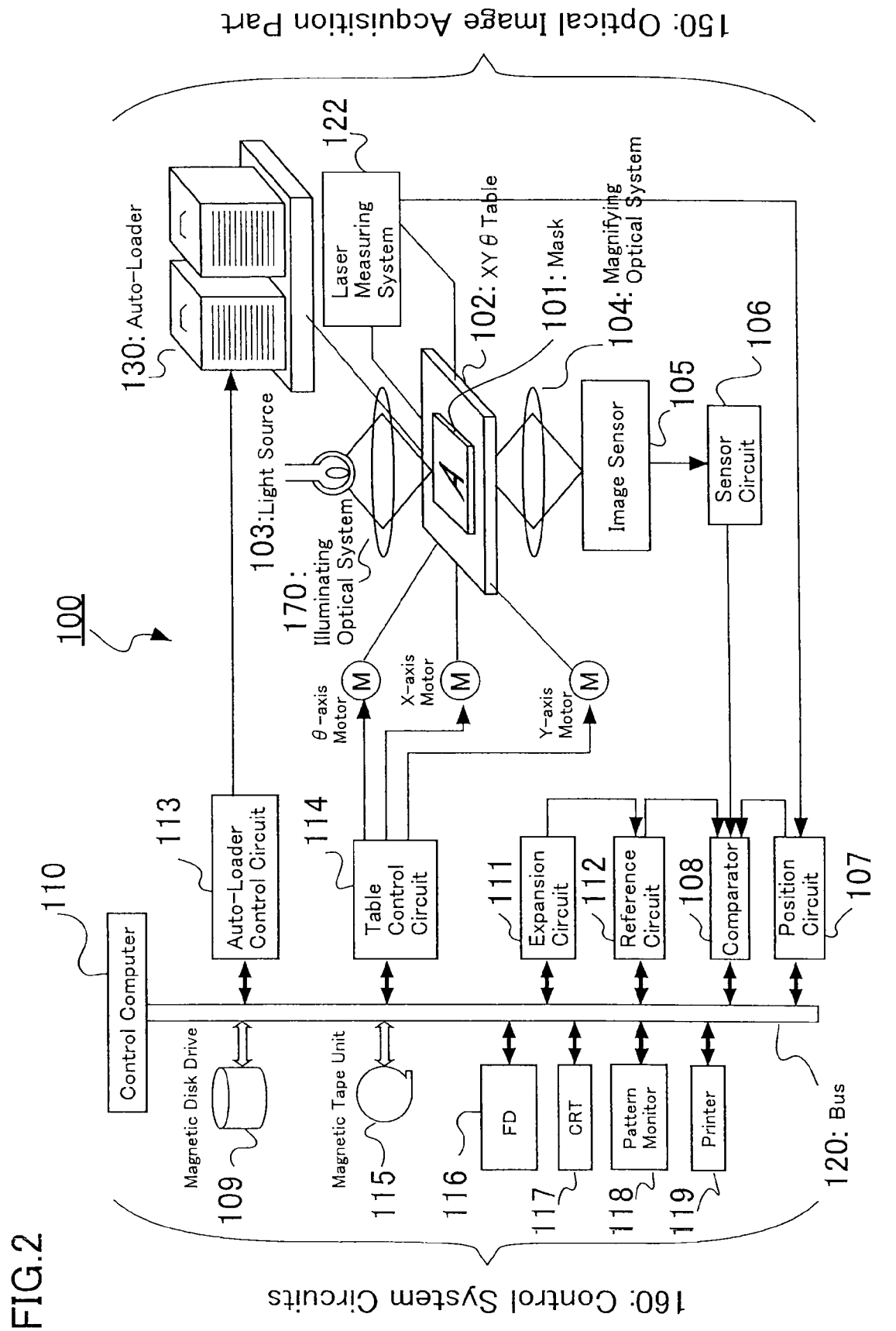
FIG. 2 is a block diagram of a mask inspection apparatus in the first embodiment.

FIG. 2 is a block diagram showing the configuration of a pattern inspection apparatus in the first embodiment. In FIG. 2, a pattern inspection apparatus 100 for inspecting a mask includes an optical image acquisition part 150 and control system circuits 160. The optical image acquisition part 150 includes an XYθ table 102, a light source 103, a magnifying optical system 104, an image sensor 105, a sensor circuit 106, a laser measuring system 122, an auto-loader 130, and an illuminating optical system 170.

In the control system circuits 160, a control computer 110, which is a computer, is connected to a position circuit 107, a comparator 108, an expansion circuit 111, a reference circuit 112, an auto-loader control circuit 113, a table control circuit 114, a magnetic disk drive 109, a magnetic tape unit 115, a flexible disk drive (FD) 116, a CRT 117, a pattern monitor 118, and a printer 119 via a bus 120 serving as a data transmission path. The XYθ table 102 is driven by an X-axis motor, Y-axis motor and θ-axis motor.

FIG. 2 omits components other than those needed to describe the present embodiment. It is needless to say that the pattern inspection apparatus 100 normally includes other necessary components.

Operations of the pattern inspection apparatus 100 will be described below with reference to FIG. 2. First, the optical image acquisition part 150 acquires an optical image of a mask 101 on which a pattern is formed based on design data to serve as a target object. More specifically, an optical image is acquired as described blow.

The mask 101 is put on the XYθ table 102 that moves in horizontal and rotational directions by the X-axis, Y-axis, and θ-axis motors. Then, a pattern formed on the mask 101 is irradiated with light by the appropriate light source 103 arranged above the XYθ table 102.

A luminous flux shone from the light source 103 is shone on the mask 101 via the illuminating optical system 170. The magnifying optical system 104, the image sensor 105, and the sensor circuit 106 are arranged below the mask 101. Then, the light that passes through the mask 101 is formed as an optical image on the image sensor 105 via the magnifying optical system 104. The magnifying optical system 104 may automatically be focused by an automatic focusing mechanism (not shown).

Figure 3:
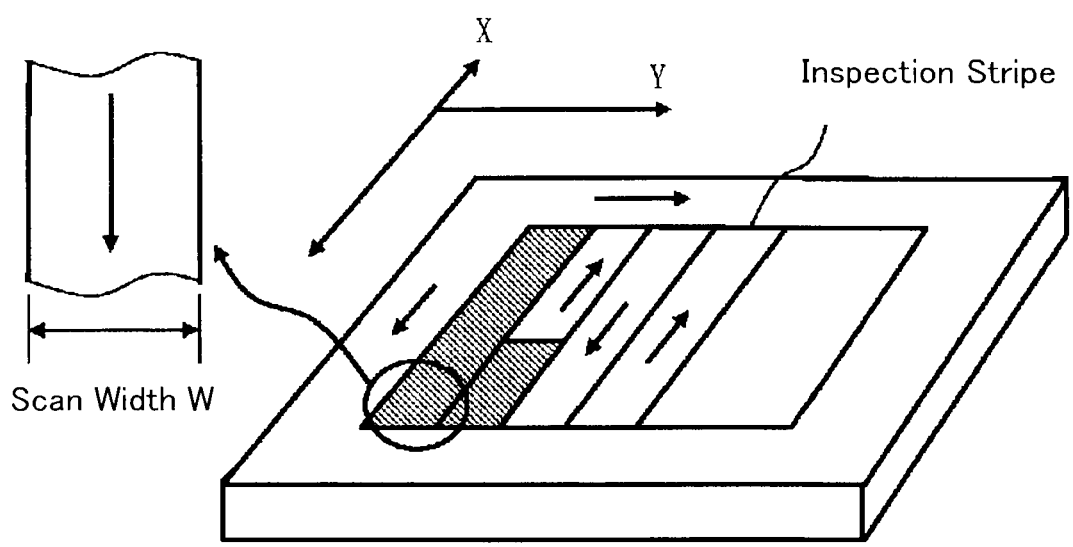
FIG. 3 is a diagram for illustrating a procedure for acquiring an optical image in the first embodiment.

FIG. 3 is a diagram for illustrating a procedure for acquiring an optical image. As shown in FIG. 3, an inspected region is virtually divided into a plurality of rectangular inspection stripes having a scan width W in the Y direction. Then, the operation of the XYθ table 102 is controlled in such a way that the divided inspection stripes are further scanned continuously to acquire an optical image while moving in the X direction.

Images of the scan width W shown in FIG. 3 are continuously input into the image sensor 105 (FIG. 2). After an image in the first inspection stripe is acquired, an image of the scan width W in the second inspection stripe is continuously input while similarly moving in the opposite direction this time. Then, when an image in the third inspection stripe is acquired, an image is acquired while moving in a direction opposite to the direction to acquire the image in the second inspection stripe, that is, in the direction to acquire the image in the first inspection stripe. By continuously acquiring images in this manner, a wasteful processing time can be reduced.

An image of pattern formed on the image sensor 105 is photoelectric-converted by the image sensor 105 and further A/D (analog-digital)-converted by the sensor circuit 106. The image sensor 105 has, for example, a sensor like a TDI (time delay & integration) sensor of a photodiode array arranged therein. By continuously moving the XYθ table 102 serving as a stage in the X direction, the TDL sensor takes the images of the pattern of the mask 101.

The light source 103, the magnifying optical system 104, the image sensor 105, and the sensor circuit 106 constitute a high-magnification inspecting optical system. In addition to a photodiode array, a CMOS sensor, CCD sensor and the like can be used as the image sensor 105.

The XYθ table 102 is driven by the table control circuit 114 under the control of the control computer 110. The XYθ table 102 is made movable by a driving system such as 3-axis (X-Y-θ) motors driving in the X, Y, and θ directions. Step motors, for example, can be used as these X-axis motor, Y-axis motor, and θ-axis motor.

Then, the movement position of the XYθ table 102 is measured by the laser measuring system 122 and supplied to the position circuit 107. The mask 101 on the XYθ table 102 is automatically transported from the auto-loader 130 driven by the auto-loader control circuit 113, to be automatically removed after the inspection is completed.

Measurement data (inspected pattern image data: optical image) output from the sensor circuit 106 is sent to the comparator 108 together with position data of the mask 101 on the XYθ table 102 output from the position circuit 107. Measurement data is, for example, unsigned 8-bit data and represents gradations in brightness of each pixel. Measurement data is compared, for example, in units of image data of 512 pixels× 512 pixels.

Design data used for forming a pattern on the mask 101 is stored in the magnetic disk drive 109. Then, the design data is read from the magnetic disk drive 109 into the expansion circuit 111 via the control computer 110. The expansion circuit 111 converts the read design graphic data of the mask 101 into binary or multi valued image data before the image data being sent to the reference circuit 112.

Here, the design data uses rectangles and triangles as basic figures. And the design data has graphic data defining the shape, size, position and the like of each figure with information such as coordinates (x, y) at two vertex positions of a figure and a graphic code serving as an identifier to identify the type of figures such as the rectangle and triangle. When design data is input into the expansion circuit 111, the design data is expanded into data for each figure.

Then, the graphic code showing the graphic shape of the graphic data, graphic dimensions and the like are interpreted.

Then, the data is expanded into binary or multivalued figure pattern data as a pattern arranged in grids of predetermined quantization dimensions.

In other words, design data is read and the occupancy occupied by figures for each cell obtained by virtually dividing an inspection region is calculated to generate n-bit occupancy data, which is output to an internal pattern memory. For example, one cell is preferably set as one pixel.

Then, if one pixel have the resolution of $1/2^8$ (=1/256), the occupancy in a pixel is calculated by allocating a small region of 1/256 for a portion of graphic region arranged in the pixel. Then, the occupancy is generated as 8-bit occupancy data and stored in the internal pattern memory.

The reference circuit 112 creates reference data (inspection reference pattern image data) from image data of figures sent from the expansion circuit 111 to be compared with measurement data. The reference data to be compared is created, like measurement data, as image data of 512 pixels×512 pixels.

Here, reference data is created based on design data to carry out a "die to database inspection", but the reference data is not limited to this. A "die to die inspection" can also be carried out. In that case, reference data may be created based on other measurement data (optical image) to be compared. The reference data is sent to the comparator 108.

The comparator 108 captures the reference data and measurement data. Then, the comparator 108 compares the reference data and measurement data according to a predetermined algorithm to determine whether or not there is any defect of the mask.

Here, an example in which a mask inspection is carried out by using transmitted light that has passed through the mask is described, but a mask inspection apparatus according to the first embodiment may be configured to carry out a mask inspection by using reflected light reflected by the mask.

Figure 1A:
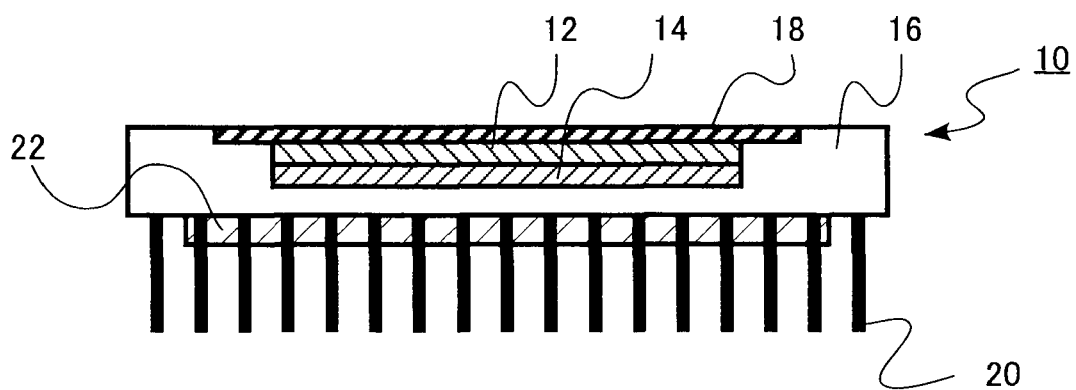
FIG. 1A and FIG. 1B are conceptual diagrams of an image sensor in a first embodiment.
Figure 1B:
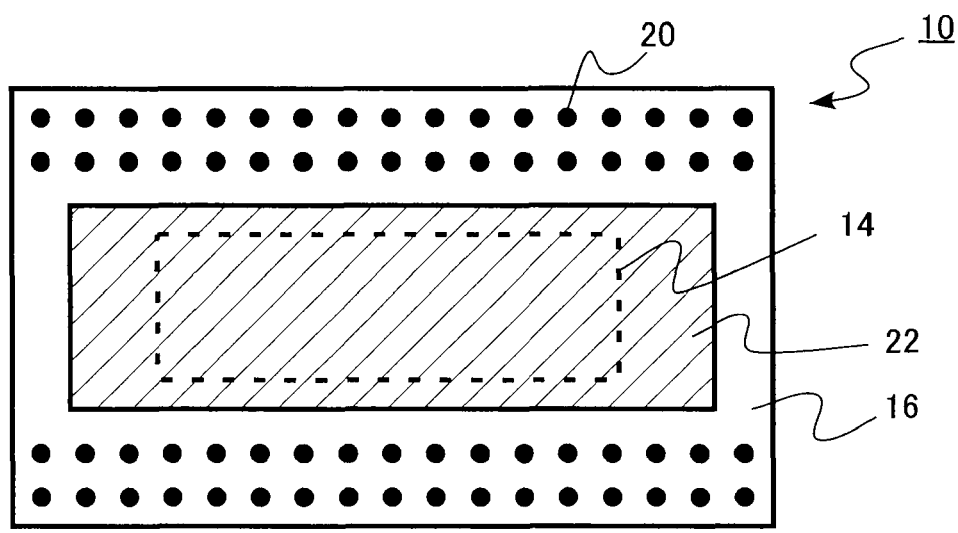

FIG. 1 is a conceptual diagram of an image sensor included in a mask inspection apparatus according to the first embodiment. FIG. 1A is a sectional view and FIG. 1B is a plan view viewed from the rear or back side.

As shown in FIG. 1, an image sensor 10 includes a sensor chip 12 such as a photodiode array, a mount bed 14 to mount the sensor chip 12, and a package 16 made of, for example, ceramic to hold the sensor chip 12 and the mount bed 14. In addition, a glass cover 18 that allows an inspection light to pass through and protects the receiving surface of the sensor chip 12 is provided on the receiving surface side of the sensor chip 12. The image sensor 10 also includes a plurality of electrode pins 20 to supply signals from the sensor chip 12 to a sensor circuit (not shown).

Further, the image sensor 10 has a radiation shielding plate 22 of heavy metal, for example, a tungsten alloy having a specific gravity equal to or greater than that of tantalum (Ta) as an environmental radiation shielding member adjacent to the package 16 on the opposite side (rear side or back side) of the receiving surface of the sensor chip.

Thus, by providing the radiation shielding plate 22 of heavy metal having a specific gravity equal to or greater than that of tantalum (Ta) on the opposite side of the receiving surface of the image sensor 10, the sensor chip 12 can efficiently be shielded from environmental radiation entering from the rear side. Therefore, noise generated by input of environmental radiation is reduced so that a false determination during mask inspection can be prevented.

Moreover, by providing the radiation shielding plate 22 at a location adjacent to the sensor chip 12, shielding of environmental radiation from a wider range can be achieved by a small area. Therefore, effective shielding of radiation can be realized with a minimum increase in weight and at low prices.

Moreover, shielding capacity of environmental radiation can be adjusted appropriately by changing the thickness of the radiation shielding plate 22.

Further, by providing the radiation shielding plate 22 of heavy metal with high thermal conductivity directly or indirectly adjacent to the sensor chip 12 physically and thermally, the radiation shielding plate 22 effectively functions also as a heat sink to cool the image sensor 10. Therefore, functioning error of the image sensor 10 and the sensor circuit (not shown) due to a temperature rise or an occurrence of optical errors due to a temperature rise in the inspection apparatus can efficiently be suppressed.

Here, for example, Ta, W, Re, Os, Ir, Pt, Au, Pb, Bi, and other alloys are applicable as heavy metal having a specific gravity equal to or greater than that of tantalum (Ta). In terms of price, however, Ta, W, Pb, or alloys are preferable. Particularly, it is preferable to apply tungsten or tungsten alloys having high radiation shielding properties and low toxicity.

As tungsten alloys, for example, an alloy containing tungsten as a main component and at least one of nickel, iron, and copper as a minor component is applicable. In terms of workability, tungsten alloys are superior to pure tungsten and thus preferable.

As shown in FIG. 1B, a plane area of the radiation shielding plate 22 is preferably larger than that of the sensor chip 12, which is indicated by a broken line rectangle. This is because effective shielding of radiation entering from the rear side of the sensor chip 12 can thereby be achieved and the radiation effect can also be increased.

Here, the radiation shielding plate 22 is described by taking an example in which the radiation shielding plate 22 is indirectly adjacent to the sensor chip 12 via the mount bed 14 and the package 16. This structure is easy and preferable in terms of the manufacture, but, for example, a structure in which the radiation shielding plate 22 is provided between the mount bed 14 and the sensor chip 12 and the radiation shielding plate 22 is directly in contact with the rear surface of the sensor chip 12 can also be adopted.

Second Embodiment

The mask inspection apparatus in the second embodiment of the present invention is the same as that in the first embodiment except that a cooling unit is provided on the rear side of an image sensor. Therefore, a description that will repeat what is described in the first embodiment is omitted.

Figure 4A:
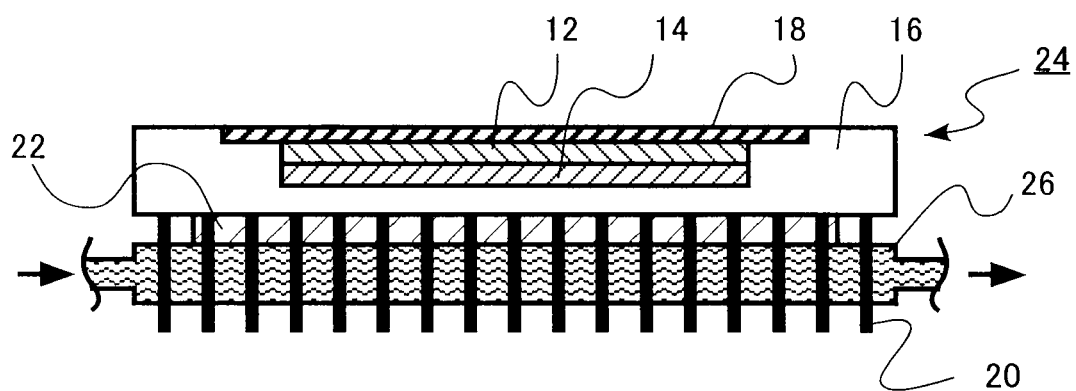
FIG. 4A and FIG. 4B are conceptual diagrams of the image sensor in a second embodiment.
Figure 4B:
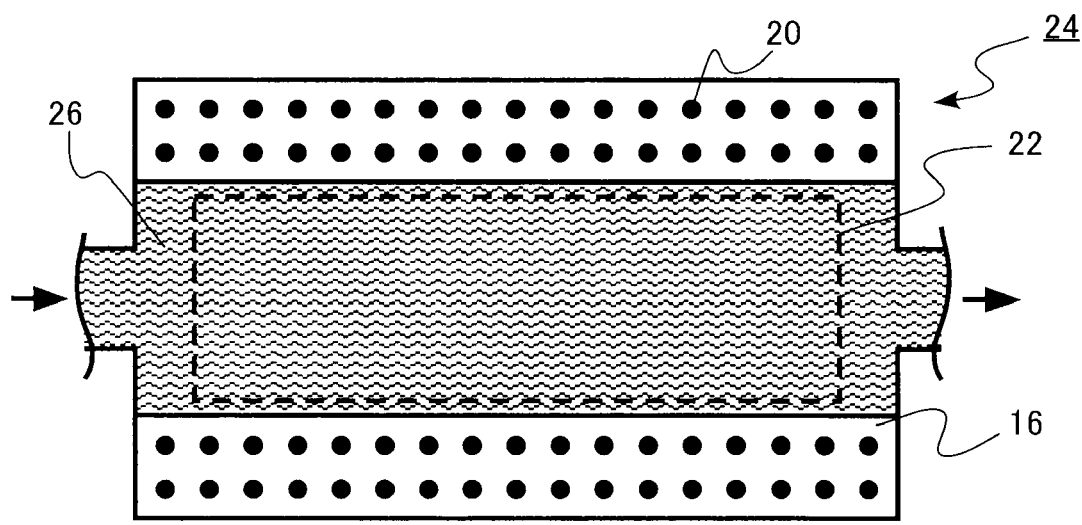

FIG. 4 is a conceptual diagram of the image sensor of the mask inspection apparatus in the present embodiment. FIG. 4A is a sectional view and FIG. 4B is a plan view viewed from the rear side. As shown in FIG. 4, an image sensor 24 includes, like the first embodiment, the sensor chip 12, the mount bed 14, the package 16, the glass cover 18, the electrode pins 20, and the radiation shielding plate 22.

Moreover, a cooling unit 26 is provided in contact with the underside of the radiation shielding plate 22. In the cooling unit 26, cooling water is made to flow in the direction shown by arrows in FIG. 4. Thus, it becomes possible to promote cooling of the image sensor 24 by absorbing heat from the radiation shielding plate 22 functioning as a heat sink. Therefore, functioning error of the image sensor 24 and the sensor circuit (not shown) due to a temperature rise or an occurrence of optical errors due to a temperature rise in the inspection apparatus can be suppressed still more efficiently.

Of environmental radiation, for example, complete shielding of neutron rays cannot be achieved by the radiation shielding plate 22 of heavy metal. Water provides high shielding properties of neutron rays. Therefore, by providing the cooling unit 26 on the underside of the radiation shielding plate 22, like the present embodiment, the shielding effect of neutron rays can be improved.

Incidentally, as shown in FIG. 4B, the plane area of the cooling unit 26 is preferably equal to or larger than that of the radiation shielding plate 22, which is indicated by a broken line rectangle. This is because absorption of heat by the radiation shielding plate 22 can thereby be improved and the radiation effect can also be increased.

Here, the cooling unit 26 is described in a cube shape as an example. The cube shape is preferable from the viewpoint of the shielding effect of neutron rays, but the shape thereof is not limited to the cube shape and, for example, a tubular cooling unit is also applicable.

Third Embodiment

In the mask inspection apparatus in the third embodiment of the present invention, the environmental radiation shielding member of heavy metal is the package of an image sensor. Moreover, an insulator is provided between the sensor chip and electrode pins of the image sensor and the package to insulate the sensor chip and electrode pins of the image sensor from the package.

The basic configuration of the mask inspection apparatus 100, selection of materials of the environmental radiation shielding member and the like are the same as those in the first embodiment. Therefore, a description that will repeat what is described in the first embodiment is omitted.

Figure 5A:
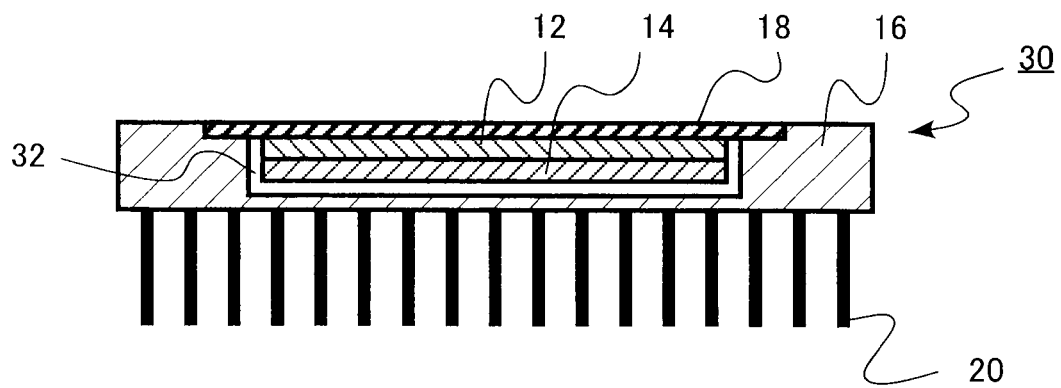
FIG. 5A and FIG. 5B are conceptual diagrams of the image sensor in a third embodiment.
Figure 5B:
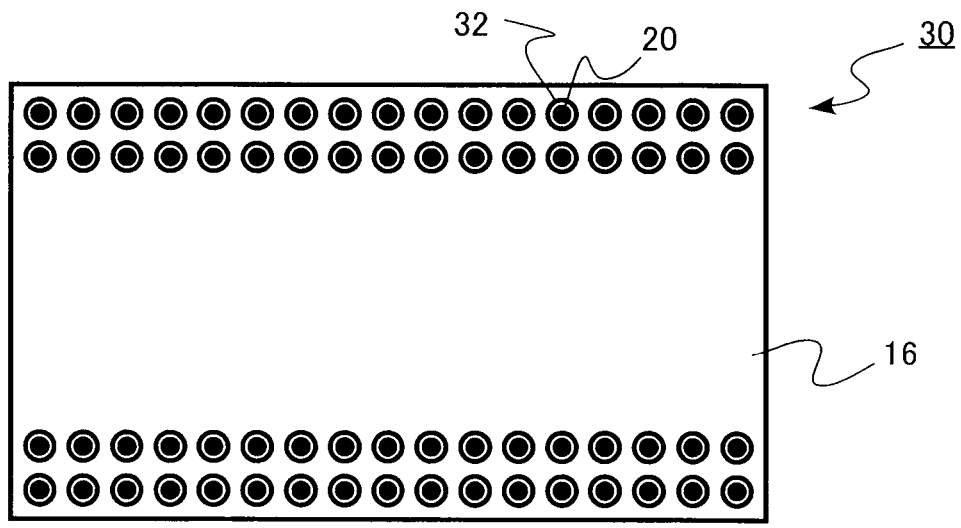

FIG. 5 is a conceptual diagram of the image sensor of the mask inspection apparatus according to the present embodiment. FIG. 5A is a sectional view and FIG. 5B is a plan view viewed from the rear side.

As shown in FIG. 5, an image sensor 30 includes the sensor chip 12 such as a photodiode array, the mount bed 14 to mount the sensor chip 12, and the package 16 made of heavy metal to hold the sensor chip 12 and the mount bed 14. In addition, the glass cover 18 that allows an inspection light to pass through and protects the receiving surface of the sensor chip 12 is provided on the receiving surface side of the sensor chip 12. The image sensor 30 also includes the plurality of electrode pins 20 to supply signals from the sensor chip 12 to the sensor circuit (not shown).

Further, an insulator 32 is provided between the sensor chip 12 and the electrode pins 20 of the image sensor 30 and the package 16 to insulate the sensor chip 12 and the electrode pins 20 of the image sensor 30 from the package 16. In this manner, the package 16 made of heavy metal, for example, a tungsten alloy is provided as an environmental radiation shielding member on the opposite side (rear side) of the receiving surface and both sides of the image sensor 30.

Thus, by forming the package 16 of the image sensor 30 from heavy metal, efficient shielding of environmental radiation entering from the rear side and both sides of the sensor chip 12 can be achieved. Therefore, noise generated by input of environmental radiation is further reduced so that a false determination during mask inspection can be prevented. In addition, by providing the package 16 itself with an environmental radiation shielding function, a mask inspection apparatus superior in radiation resistance can be provided in a simpler configuration because there is no need to provided a additional member for environmental radiation shielding.

Further, by enclosing the sensor chip 12 with heavy metal with high thermal conductivity, the package 16 itself functions effectively as a heat sink to cool the image sensor 30. Therefore, malfunctioning of the image sensor 30 or the sensor circuit (not shown) due to a temperature rise can be suppressed still more efficiently.

Fourth Embodiment

The mask inspection apparatus in the fourth embodiment of the present invention includes a light source, an illuminating optical system for irradiating a mask with an inspection light emitted from the light source, a magnifying optical system for causing the inspection light with which the mask is irradiated to form an optical image, and an image camera having an image sensor for acquiring the optical image as a photo detector, wherein a frame of the image camera is formed from heavy metal having a specific gravity equal to or greater than that of tantalum (Ta). The basic configuration of the mask inspection apparatus 100, selection of materials of the environmental radiation shielding member and the like are the same as those in the first embodiment. Therefore, a description that will repeat what is described in the first embodiment is omitted.

Figure 6:
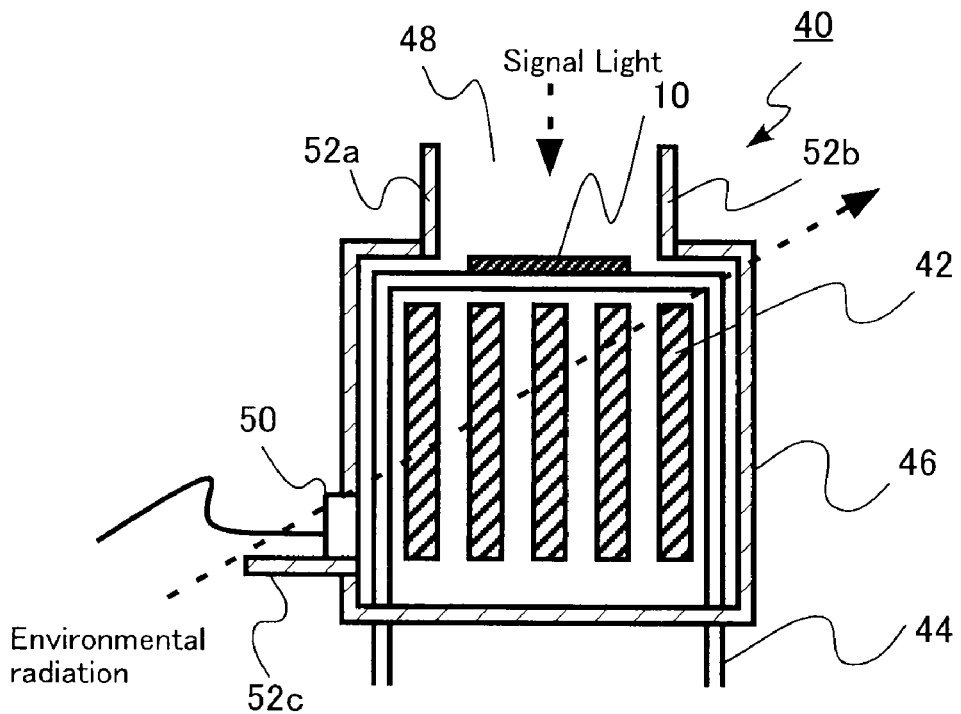
FIG. 6 is a conceptual sectional view of an image camera in a fourth embodiment.

FIG. 6 is a conceptual sectional view of an image camera of the mask inspection apparatus in the present embodiment. An image camera 40 contains the image sensor 10 having an environmental radiation shielding member of heavy metal having a specific gravity equal to or greater than that of tantalum (Ta) as a photo detector.

The image camera 40 includes a frame 46 containing a camera mechanism such as a plurality of circuit substrate 42 of a sensor circuit and a cooling water pipe 44 for a cooling unit and the like. The frame 46 is formed from heavy metal having a specific gravity equal to or greater than that of tantalum (Ta).

Thus, by forming the frame 46 itself from heavy metal having a specific gravity equal to or greater than that of tantalum (Ta), shielding of environmental radiation entering the image sensor 10 can be achieved. Particularly, only replacement of the existing material of the camera frame is needed and thus, no spatial restriction inside the camera is imposed, making internal design changes unnecessary.

Moreover, since the change of thickness of the frame 46 of a camera has a higher degree of flexibility than, for example, that of the environmental radiation shielding member provided in the image sensor 10 and thus, the thickness of the frame 46 can easily be changed in accordance with necessary shielding capacity. In addition, heavy metal having a higher specific gravity is provided only in the camera. Therefore, environmental radiation shielding can be realized at lower prices and in more reduced weight than by widely wrapping a camera fulcrum outside the camera, a pump unit for cooling, a circuit substrate excluding the sensor circuit and the like.

In the frame 46, for example, a window 48 for incident light (or signal light), a socket unit 50 for power supply, and an opening part such as a tapped hole are provided. There is a cause for concern that environmental radiation (dotted line arrow in FIG. 6) entering through the opening part could reach the image sensor 10. To prevent such environmental radiation from reaching the image sensor 10, it is effective to provide environmental radiation shielding projections 52a, 52b, and 52c formed from heavy metal having a specific gravity equal to or greater than that of tantalum (Ta). Regarding the tapped hole, shielding of environmental radiation becomes possible by forming a screw itself from heavy metal having a specific gravity equal to or greater than that of tantalum (Ta).

Heat generated during operation of the mask inspection apparatus is released not only from the main body of the image sensor 10, but also from all electric systems such as the circuit substrates 42 of the sensor circuit and heat not controlled by the cooling unit is transmitted to the frame 46. Therefore, by using heavy metal with high thermal conductivity for the frame 46, heat can efficiently be released to the outside and the cooling effect of the image camera is improved. Thus, functioning error of the image sensor 10 and the sensor circuit due to a temperature rise or an occurrence of optical errors due to a temperature rise in the inspection apparatus can be suppressed still more efficiently.

The present embodiment is described by taking an example in which the image sensor 10 having an environmental radiation shielding member of heavy metal having a specific gravity equal to or greater than that of tantalum (Ta) described in the first to third embodiments is a photo detector. This is preferable because shielding ability is improved by double environmental radiation shielding. Also, this is preferable because the cooling efficiency of the image camera is improved by the double cooling mechanism. However, that the image sensor 10 has an environmental radiation shielding member is not required and it is needless to say that forming the frame 46 from heavy metal having a specific gravity equal to or greater than that of tantalum (Ta) alone can achieve an effect of improving environmental radiation shielding and cooling efficiency.

Fifth Embodiment

In the mask inspection apparatus in the fifth embodiment of the present invention, a second environmental radiation shielding member filled with water is provided in contact with the outer surface of the frame of the image camera having the image sensor as a photo detector described in the first to third embodiments.

The basic configuration of the mask inspection apparatus 100, selection of materials of the environmental radiation shielding member and the like are the same as those in the first embodiment. Therefore, a description that will repeat what is described in the first embodiment is omitted.

Figure 7:
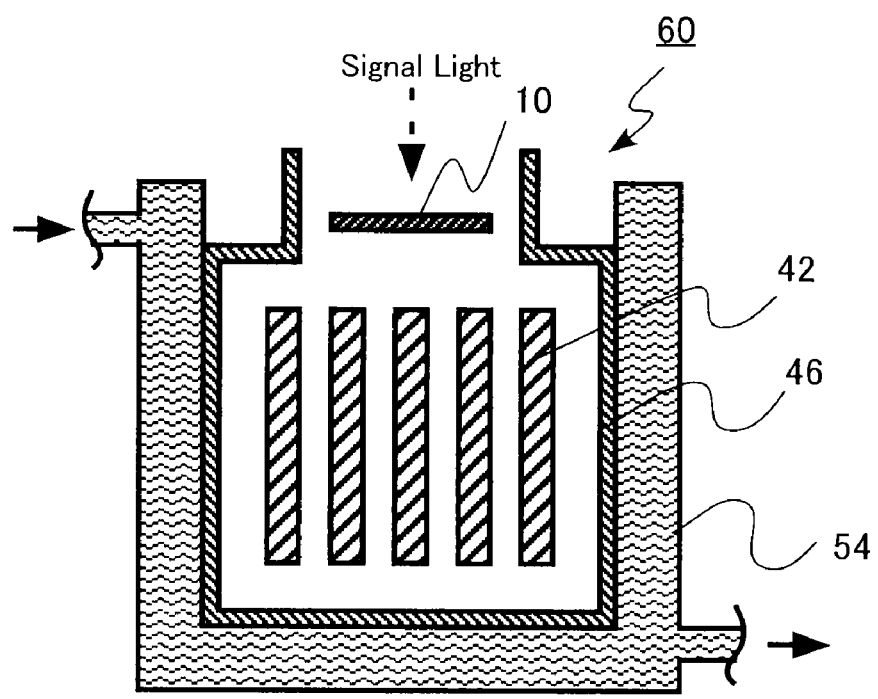
FIG. 7 is a conceptual sectional view of the image camera in a fifth embodiment.

FIG. 7 is a conceptual sectional view of an image camera of the mask inspection apparatus in the present embodiment. An image camera 60 has the image sensor 10 as a photo detector and includes the frame 46 containing a camera mechanism such as the circuit substrate 42 of the sensor circuit.

Further, a water-cooling bath 54, which is the second environmental radiation shielding member filled with water, is provided in contact with the outer surface of the frame of the image camera. In the water-cooling bath 54, cooling water is made to flow in the direction shown by arrows in FIG. 7.

In the present embodiment, the image camera 60 is enclosed with water having high shielding properties of neutron rays that are difficult to achieve shielding by an environmental radiation shielding member of heavy metal. Accordingly, shielding of neutron rays entering the image sensor 10 is realized so that a mask inspection apparatus particularly superior in radiation resistance to neutron rays can be provided. In addition, because the shape and size design of the water-cooling bath 54 have a high degree of flexibility, when compared with the second embodiment, it becomes possible to set an appropriate shape and size for radiation shielding.

Further, by providing the water-cooling bath 54 around the camera mechanism such as the circuit substrate 42 to be a source of heat generation, functioning error of the image sensor 10 and the sensor circuit (not shown) due to a temperature rise or an occurrence of optical errors due to a temperature rise in the inspection apparatus can be suppressed still more efficiently.

Sixth Embodiment

Figure 8:
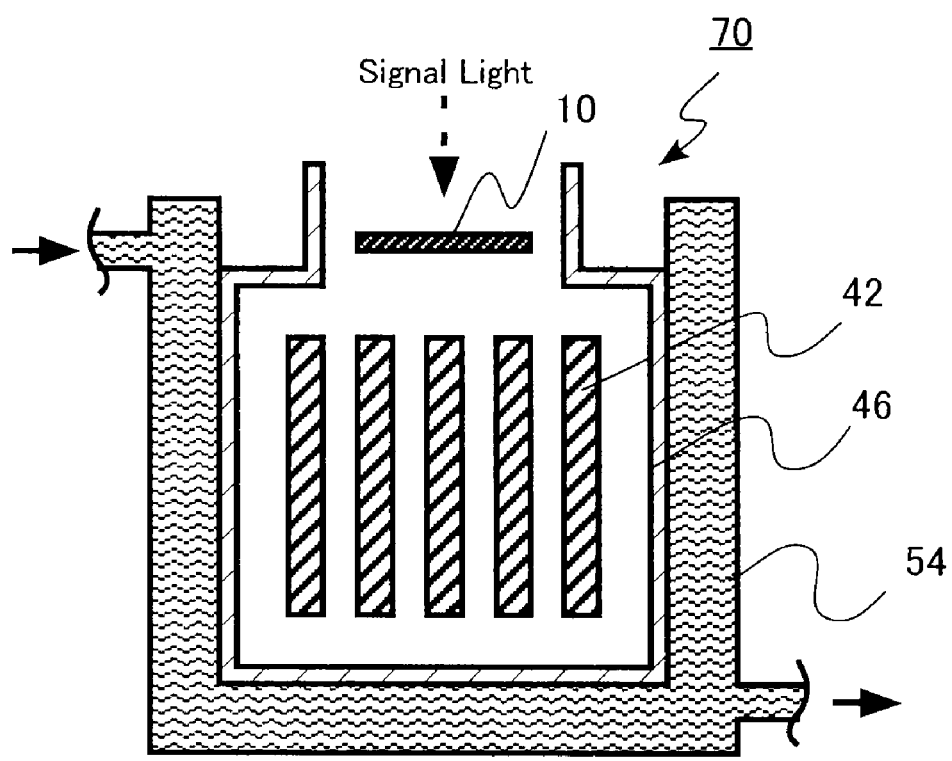
FIG. 8 is a conceptual sectional view of the image camera in a sixth embodiment.

The mask inspection apparatus in the sixth embodiment of the present invention has a configuration, as shown in FIG. 8, combining the fourth embodiment and the fifth embodiment. That is, the frame 46 of an image camera 70 is formed from heavy metal having a specific gravity equal to or greater than that of tantalum (Ta). In addition, the water-cooling bath 54, which is the second environmental radiation shielding member filled with water, is provided in contact with the outer surface of the frame 46.

According to a mask inspection apparatus in the present embodiment, $\alpha$ rays, $\beta$ rays, $\gamma$ rays, and X rays of environmental radiation are effectively shielded by heavy metal and neutron rays by a water-cooling bath. In addition, an extremely excellent cooling effect can be realized by heavy metal with high thermal conductivity and a water-cooling bath. Thus, a mask inspection apparatus that presents functioning error/false determination involved in environmental radiation or a temperature rise can be provided.

In the foregoing, embodiments have been described with reference to concrete examples. However, the present invention is not limited to these concrete examples. For example, while a transmitted light is used in each embodiment, a reflected light may be used or both a transmitted light and a reflected light at the same time.

While a reference image is generated from design data, data of the same pattern imaged by an image sensor may also be used. In other words, whether a die to die inspection or a die to database inspection does not matter.

While a description of portions that are not directly used to describe the present invention such as the apparatus configuration and control techniques is omitted, the needed apparatus configuration or control techniques can appropriately be selected and used. In addition, all mask inspection apparatuses including elements of the present invention and whose design can appropriately be modified by persons skilled in the art are included in the scope of the present invention.

What is claimed is:

1. A mask inspection apparatus, comprising:
   a light source;
   an illuminating optical system configured to irradiate a mask with an inspection light emitted from the light source;
   a magnifying optical system configured to cause the inspection light with which the mask is irradiated to form an optical image; and
   an image sensor configured to acquire the optical image, wherein,
   the image sensor has an environmental radiation shielding member of heavy metal having a specific gravity equal to or greater than that of tantalum (Ta) at least on a side of a package opposite to a receiving surface of a sensor chip which receives the optical image,
   the environmental radiation shielding member is in contact with the package of the image sensor, and
   a plane area of the environmental radiation shielding member is larger than a plane area of the image sensor and smaller than a plane area of the package.

2. A mask inspection apparatus, comprising:
   a light source;
   an illuminating optical system configured to irradiate a mask with an inspection light emitted from the light source;
   a magnifying optical system configured to cause the inspection light with which the mask is irradiated to form an optical image; and an image sensor configured to acquire the optical image, wherein, the image sensor has an environmental radiation shielding member of heavy metal having a specific gravity equal to or greater than that of tantalum (Ta) at least on a side of a package opposite side to a receiving surface of a sensor chip which receives the optical image, the environmental radiation shielding member is in contact with the package of the image sensor, and an insulator is provided between the sensor chip and the package, and between electrode pins of the image sensor and the package, to insulate the sensor chip and the electrode pins of the image sensor from the package.

3. The mask inspection apparatus according to claim 1, wherein the heavy metal is tungsten (W) or tungsten alloys.

4. The mask inspection apparatus according to claim 1, further comprising:

a water-cooling unit on a back side of the image sensor.

5. The mask inspection apparatus according to claim 1, further comprising:

a water-cooling unit on a back side of the image sensor sandwiching the environmental radiation shielding member between the image sensor and the water-cooling unit.

6. The mask inspection apparatus according to claim 1, further comprising:

a second environmental radiation shielding member filled with water being provided in contact with an outer surface of a frame of an image camera having the image sensor as a photo detector.

7. A mask inspection apparatus, comprising:

a light source;

an illuminating optical system configured to irradiate a mask with an inspection light emitted from the light source;

a magnifying optical system configured to cause the inspection light with which the mask is irradiated to form an optical image; and an image camera having a frame containing an image sensor configured to acquire the optical image, and a circuit substrate of a sensor circuit, wherein an environmental radiation shielding member of a heavy metal having a specific gravity equal to or greater than that of tantalum (Ta) is provided at least on a side of a package opposite to a receiving surface of a sensor chip of the image sensor which receives the optical image and an image sensor side of the circuit substrate.

8. The mask inspection apparatus according to claim 7, wherein the heavy metal is tungsten (W) or tungsten alloys.

9. The mask inspection apparatus according to claim 7, wherein the environmental radiation shielding member of the heavy metal has the specific gravity equal to or greater than that of tantalum (Ta) at least on an opposite side of a receiving surface of a sensor chip.

10. The mask inspection apparatus according to claim 9, wherein the environmental radiation shielding member is tungsten (W) or tungsten alloys.

11. The mask inspection apparatus according to claim 9, wherein the environmental radiation shielding member is provided in contact with a package of the image sensor.

12. The mask inspection apparatus according to claim 9, wherein, the environmental radiation shielding member is a package of the image sensor, and an insulator is provided between the sensor chip and the package, and electrode pins and the package to insulate the sensor chip and the electrode pins of the image sensor from the package.

13. The mask inspection apparatus according to claim 7, further comprising:

a water-cooling unit on a back side of the image sensor.

14. The mask inspection apparatus according to claim 11, further comprising:

a water-cooling unit on a back side of the image sensor sandwiching the environmental radiation shielding member between the image sensor and the water-cooling unit.

15. The mask inspection apparatus according to claim 11, wherein a plane area of the environmental radiation shielding member is larger than that of the sensor chip.

16. The mask inspection apparatus according to claim 7, further comprising:

a second environmental radiation shielding member filled with water being provided in contact with an outer surface of the frame.

\* \* \* \* \*